United States Patent [19]

Virgilio et al.

[11] Patent Number: 4,564,714

[45] Date of Patent: Jan. 14, 1986

[54] PROCESS FOR THE PREPARATION OF 2,4,5-TRICHLOROPHENOL UNDER ACIDIC CONDITIONS

[75] Inventors: Joseph A. Virgilio, Wayne; Joachim E. Freudewald, Basking Ridge, both of N.J.

[73] Assignee: Givaudan Corporation, Clifton, N.J.

[21] Appl. No.: 666,411

[22] Filed: Oct. 30, 1984

[51] Int. Cl.$^4$ .............................................. C07C 39/32
[52] U.S. Cl. .................................... 568/776; 568/779
[58] Field of Search ........................ 568/776, 779, 774

[56] References Cited

U.S. PATENT DOCUMENTS

| | | | |
|---|---|---|---|
| 3,920,757 | 11/1975 | Watson | 568/779 |
| 4,160,114 | 7/1979 | Shelton et al. | 568/779 |
| 4,237,321 | 12/1980 | Cuthbertson | 568/779 |
| 4,277,629 | 7/1981 | Binns et al. | 568/779 |
| 4,345,097 | 8/1982 | Howard et al. | 568/776 |
| 4,346,248 | 8/1982 | Deavenport et al. | 568/776 |

OTHER PUBLICATIONS

Watson, Tetrahedron Letters No. 30, pp. 2591–2594, (1976), Pergamon Press, Great Britain.

Primary Examiner—Werren B. Lone
Attorney, Agent, or Firm—Robert F. Tavares

[57] ABSTRACT

A novel process for the preparation of 2,4,5-trichlorophenol which comprises selectively chlorinating 2,5-dichlorophenol under acidic conditions.

11 Claims, No Drawings

PROCESS FOR THE PREPARATION OF 2,4,5-TRICHLOROPHENOL UNDER ACIDIC CONDITIONS

BACKGROUND OF THE INVENTION

The conventional industrial method for preparing 2,4,5-trichlorophenol (TCP) involves the reaction of 1,2,4,5-tetrachlorobenzene with methanolic or aqueous, methanolic sodium hydroxide at high temperatures (ca. 180° C. to 190° C.). The disadvantage of such a process is that the combination of high temperature and alkalinity result in the formation of small amounts of 2,3,7,8-tetrachlorobenzodioxin (TCDD), one of the most toxic chemicals known. Even under the most stringent conditions, levels of 100 ppb or higher of TCDD may be formed and be present in the TCP. The presence of TCDD produced in the manufacture of TCP has been a major environmental concern and has virtually led to the non-use of the herbicide known as 2,4,5-T, a derivative of TCP.

If the benefits provided by the many useful products made from TCP are to continue to be produced there is a need for a process which provides TCP which is essentially free of TCDD (i.e. no TCDD is detectable by analytical tests that are sensitive to 1 part per billion). This invention provides such a process.

SUMMARY OF THE INVENTION

The process of this invention produces TCP, essentially free of TCDD, under acidic conditions and low temperatures. It is the surprising and unexpected finding of this invention that 2,5-dichlorophenol can be selectively chlorinated by sulfuryl chloride in the presence of concentrated sulfuric acid and a catalytic amount of a sulfur catalyst. The reaction can be illustrated as follows:

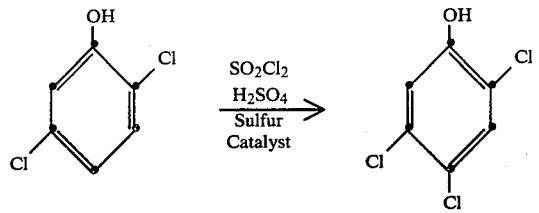

DESCRIPTION OF THE PREFERRED EMBODIMENTS

The reaction, simply described, is the monochlorination of 2,5-dichlorophenol in the 4-position with sulfuryl chloride in sulfuric acid in the presence of a sulfur catalyst. Without a sulfur catalyst, the reaction is relatively slow and not very selective. In the presence of the sulfur catalyst, however, the chlorination is rapid and highly selective.

The success of this reaction depends on using a set of conditions that produce the desired result while suppressing certain undesirable side reactions. It is preferred to use one mole or more of sulfuryl chloride per mole of 2,5-dichlorophenol to be reacted. Less than one mole results in the presence of unreacted 2,5-dichlorophenol in the final product. A slight excess of sulfuryl chloride, about 10 percent, may be used to insure that all the starting material is consumed. An excess greater than 30 percent is not recommended. Such excess leads to chlorination of the 2,4,5-trichlorophenol to 2,3,4,6-tetrachlorophenol resulting in lower yields of the desired product.

It is preferred to use concentrated sulfuric acid. While concentrations as low as 70 percent are suitable, better results are obtained when the acid is more concentrated, e.g. 80 to 100 percent. The best results are obtained using concentrations of 85 to 98 percent and this is the preferred range. It is more practical and therefore especially preferred to use the commercially available grades of concentrated sulfuric acid which range from about 93 to 96 percent.

The amount of sulfuric acid present does not appear to be critical, although it is advantageous to use at least a one to one weight ratio of sulfuric acid to 2,5-dichlorophenol to allow for proper mixing and fluidity for agitation. A ratio of 1.7 to 1 seems optimal. Ratios as high as 5 to 1 provide good results but the extra amount of acid seems to provide no advantage in terms of selectivity or yield.

The presence of sulfur catalyst is critical. While any sulfur containing organic compound or elemental sulfur has a beneficial effect, those compounds having an aromatic ring bound to the sulfur appear to work best, with diaryl sulfides yielding the best selectivity and reaction rate.

Any diaryl sulfide would be suitable. Diphenyl sulfide is especially preferred because it is the most readily available and most economical of the diaryl sulfides.

The amount of sulfide used is not critical. Suitable results can be obtained with small amounts of catalyst. It is preferred to use about 0.3 to 2.0 grams of catalyst per mole of 2,5-dichlorophenol. Larger amounts of catalyst may be used, but any catalyst in excess of 2.0 grams per mole of 2,5-dichlorophenol, while not detrimental, appears to offer no additional advantage.

A suitable temperature range is between −10° C. and 25° C. Below −40° C. the reaction mixture begins to freeze and temperatures below −40° C. are not practical. At temperatures above 25° C., the competition between sulfonation and chlorination becomes an important factor and produces much lower yields of desired product. It is preferred to keep the temperature below 20° C. with temperatures between 0° C. and 15° C. being the most practical and especially preferred.

Additional adjuvants may be used. It is felt that small amounts of aluminum chloride may have a positive accelerating or kinetic effect on the reaction. However, good selectivity is obtained without aluminum chloride. It has also been found that dimethylsulfoxide is helpful in providing additional fluidity and mixing in the reaction mixture. The absence of dimethylsulfoxide does not, however, appear to have any detrimental effect on the selectivity of the reaction.

The reaction can be run simply by mixing the required reagents at the desired temperature. Since the reaction is exothermic, it is preferred to control the reaction by adding at least one of the reactants to the reaction vessel containing the sulfuric acid and the catalyst.

The order of addition does not appear to be critical. Good results are obtained when either reagent (sulfuryl chloride or 2,5-dichlorophenol) is added to all the other reagents, or when both are added to the sulfuric acid and the catalyst. Slightly better results appear to be obtained when the 2,5-dichlorophenol is added to the reaction mixture containing the sulfuryl chloride, the sulfur catalyst and the sulfuric acid.

The rate of addition is not critical and depends on both batch size and the efficiency of the cooling, 30 to 60 minutes being typical for a laboratory run. The reaction is then stirred an additional time, about 1 to 2 hours. (The progress of the reaction can be followed by working up a small sample and analyzing by gas-liquid chromatography using the column and conditions described in Example 2.) The reaction may be heated for an additional hour at 60° to 70° C. to sulfonate any unreacted 2,5-dichlorophenol, if desired.

The reaction product can be isolated from the sulfuric acid mixture by any suitable method such as quenching the sulfuric acid mixture on ice and extracting with a suitable solvent, or adding a suitable solvent to the cooled reaction mixture and removing the solvent layer. (This latter procedure allows the sulfuric acid to be recovered and reused in a subsequent reaction.) A suitable solvent would be any solvent that would be insoluble in the acid layer, would be acid stable and would solubilize the 2,4,5-trichlorophenol formed, e.g. hydrocarbons (aliphatic and aromatic) or chlorinated hydrocarbons (e.g. chloroform, ethylene dichloride or the like). The choice of solvent is not critical and would depend on what was to be done with the TCP.

For example where the 2,4,5-trichlorophenol solution is to be used directly in the manufacture of another product, it may be preferred to use a suitable solvent for the subsequent reaction and add the solution directly. The extracted 2,4,5-trichlorophenol solution should be washed neutral before it is used directly to prepare any subsequent 2,4,5-trichlorophenol derivatives such as hexachlorophene, 2,4,5-T, etc.

Alternatively the 2,4,5-trichlorophenol can be isolated by simply removing the solvent, preferably under slightly reduced pressure. High temperatures and distillation should be avoided to avoid formation of TCDD.

ILLUSTRATION OF PREFERRED EMBODIMENTS

EXAMPLE 1

Sulfuric acid (93 percent) (150 ml) and diphenyl sulfide (0.5 g) were placed in a one liter flask and cooled to 5°–10° C. using an ice-water bath. 2,5-Dichlorophenol (50 g) was melted (55°–56° C.) and dissolved in sulfuryl chloride (50 g). This mixture was added over a period of 30 to 60 minutes to the reaction mixture which was being maintained at 5°–10° C. with an ice-water bath. After about 15 to 30 minutes a thick paste precipitated (2,4,5-trichlorophenol). The reaction was stirred for an additional two hours then heated to 60° to 70° C. for an additional hour to sulfonate any unreacted 2,5-dichlorophenol.

The reaction mixture was cooled to room temperature and extracted with 200 ml of ethylene dichloride. The ethylene dichloride layer (top layer) was separated and washed with water (200 ml) and 5 percent sodium bicarbonate (100 ml). The ethylene dichloride was removed on a rotary evaporator under reduced pressure and the resulting product was weighed and analyzed for content by gas chromatography (see Example 2, Table I, footnote a). Weight yield: 58.5 g. Analysis: (trace) 2,5-dichlorophenol; (0.6%) 2,3,6-trichlorophenol; (6.3%) 2,3,4,6-tetrachlorophenol; (93.1%) 2,4,5-trichlorophenol.

EXAMPLES 2–9

Examples 2 through 9 were run in the same manner as example 1 with the inclusion of dimethyl sulfoxide and aluminum chloride as adjuvants. Aluminum chloride (1.5 g) was added to the one liter flask with the sulfuric acid and diphenyl sulfide. Dimethyl sulfoxide (15 g) was added dropwise (slight exotherm) to the above mixture followed by the addition of the 2,5-dichlorophenol and sulfuryl chloride. The reaction mixture was maintained at 10° C. throughout.

In each of these examples one of the reaction components, or one of the reaction conditions was varied to illustrate what effect, if any, such variation had on the selectivity of the reaction and the conversion of 2,5-dichlorophenol. The other components and/or conditions remained as given above and in example 1.

EXAMPLE 2

In this example the amount of diphenyl sulfide was varied. The results of these experiments are shown in Table I. It can clearly be seen that without the sulfide catalyst the yield is extremely low and the selectivity is extremely poor.

The presence of only 0.1 g of the diphenyl sulfide results in a dramatic improvement. The amount of unreacted starting material is very small and the amount of desired product is better than 90 percent. An increase to 0.3 g of diphenyl sulfide increases the selectivity even more, providing a yield of 96 percent desired product. Higher amounts of diphenyl sulfide do not appear to provide any additional benefit.

TABLE I

| Diphenyl Sulfide (g) | Weight Yield (g) | Percent[a] | | | |
|---|---|---|---|---|---|
| | | A | B | C | D |
| — | 5.1 | 83.4 | 4.8 | 1.2 | 10.6 |
| 0.1 | 58.9 | 0.3 | 2.1 | 5.5 | 92.1 |
| 0.3 | 62.0 | trace | 1.4 | 2.5 | 96.1 |
| 0.6 | 61.8 | trace | 1.4 | 2.5 | 96.1 |
| 1.0 | 61.7 | trace | 0.6 | 2.5 | 96.1 |

[a]Composition determined by gas chromatography on a 6 ft 3% FFAP (Free Fatty Acid Phase) column at 190° C. isothermally and on a 6 ft 5% SE-30 column at 112° to 210° C. at a rate of 10° C./min.
A: 2,5-Dichlorophenol
B: 2,3,6-Trichlorophenol
C: 2,3,4,6-Tetrachlorophenol
D: 2,4,5-Trichlorophenol

EXAMPLE 3

In this example the concentration of sulfuric acid was varied. An additional run in 20% oleum was also tried. The results in Table II show clearly that the amount of sulfuric acid does not seriously affect the selectivity and that one still gets good selectivity using 80 percent sulfuric acid. It is surmised that oleum at 10° C. is probably too powerful a sulfonating agent inasmuch as the use of oleum resulted in no isolatable chlorinated phenols.

TABLE II

| H$_2$SO$_4$ Volume (ml) | Conc. (%) | Weight Yield (g) | Percent[a] | | | |
|---|---|---|---|---|---|---|
| | | | A | B | C | D |
| 150 | 80 | 61.4 | trace | 10.2 | 2.0 | 87.8 |
| 150 | 85 | 62.0 | trace | 4.8 | 2.0 | 93.2 |
| 25 | 93 | 60.4 | 1.0 | 6.6 | 2.5 | 89.9 |
| 50 | 93 | 59.9 | trace | 3.0 | 2.0 | 95.0 |
| 100 | 93 | 61.5 | trace | 2.0 | 2.0 | 96.0 |
| 150 | 20% oleum | —[b] | — | — | — | — |

[a]See Table I, Footnote a.
[b]No reaction product.

EXAMPLE 4

The amount of sulfuryl chloride was varied in this example. Table III clearly shows that the use of one mole of sulfuryl chloride per mole of dichlorophenol provides the desired product in high yield and good selectivity. The use of a slight excess, i.e., about 1.1 mole per mole of dichlorophenol also provides excellent results.

As the concentration of sulfuryl chloride increases, over-chlorination occurs, i.e., the 2,4,5-trichlorophenol becomes chlorinated to form more 2,3,4,6-tetrachlorophenol. The 2,3,4,6-tetrachlorophenol present becomes unacceptably high when the ratio of sulfuryl chloride to dichlorophenol significantly exceeds 1.3 to 1.

TABLE III

| $SO_2Cl_2$ Weight (g) | Mole Ratio[a] | Weight Yield (g) | Percent[b] A | B | C | D |
|---|---|---|---|---|---|---|
| 40 | 1.0 | 60.8 | 1.3 | 3.6 | <1.0 | 95.1 |
| 45 | 1.1 | 61.5 | trace | 0.6 | 2.5 | 96.0 |
| 50 | 1.2 | 61.0 | trace | 0.6 | 5.0 | 94.4 |
| 55 | 1.3 | 62.0 | trace | 2.1 | 8.5 | 89.4 |
| 60 | 1.5 | 62.3 | trace | 2.2 | 21.6 | 76.1 |

[a] Moles of $SO_2Cl_2$ per mole of 2,5-dichlorophenol.
[b] See Table I, Footnote a.

EXAMPLE 5

In this example the amount of aluminum chloride was varied. The results in Table IV show that the amount of aluminum chloride has little or no effect on the selectivity of the reaction.

TABLE IV

| $AlCl_3$ (g) | Weight Yield (g) | Percent[a] A | B | C | D |
|---|---|---|---|---|---|
| — | 61.1 | trace | 2.7 | 2.5 | 94.8 |
| 0.1 | 61.6 | trace | 2.3 | 2.5 | 95.2 |
| 0.3 | 61.2 | trace | 2.3 | 2.5 | 95.2 |
| 0.6 | 61.2 | trace | 1.1 | 2.5 | 96.4 |
| 1.0 | 61.9 | trace | 1.2 | 2.5 | 96.3 |

[a] See Table I, Footnote a.

EXAMPLE 6

In this example the amount of dimethyl sulfoxide was varied. Table V shows that the use of dimethyl sulfoxide has little effect on the yield of 2,4,5-trichlorophenol or on the selectivity of the reaction.

TABLE V

| Dimethyl Sulfoxide (g) | Weight Yield (g) | Percent[a] A | B | C | D |
|---|---|---|---|---|---|
| — | 60.4 | trace | 0.5 | 6.0 | 93.5 |
| 5 | 61.7 | trace | 1.0 | 1.5 | 97.4 |
| 10 | 62.0 | trace | 1.6 | 2.5 | 95.8 |
| 15 | 61.0 | trace | 0.6 | 2.5 | 96.9 |
| 20 | 61.6 | trace | 1.4 | 2.5 | 96.1 |
| 25 | 61.6 | 0.6 | 0.9 | 1.5 | 97.0 |
| 40 | 62.2 | trace | 1.6 | 2.5 | 95.8 |

[a] See Table I, Footnote a.

EXAMPLE 7

A number of sulfides were tested which were not diaryl sulfides. In these tests, the reaction was held at 10° C. for three hours instead of two hours as indicated in the general procedure. As Table VI shows, most of the sulfides and even elemental sulfur have a beneficial effect over those reactions that use no catalyst at all. It should also be noted that the yield and selectivity is very poor when compared to the use of a diarylsulfide.

TABLE VI

| Sulfide | (g) | Weight Yield (g) | Percent[a] A | B | C | D |
|---|---|---|---|---|---|---|
| $(n-Bu)_2S$ | (0.5) | 7.2 | 68.5 | 10.2 | 0.7 | 20.6 |
| $(t-Bu)_2S$ | (0.5) | 8.1 | 62.8 | 8.3 | 0.8 | 28.1 |
| $(CH_3(CH_2)_{11})_2S$ | (0.5) | 10.4 | 74.7 | 6.4 | 1.6 | 17.3 |
| $(benzyl)_2S$ | (0.5) | 35.3 | 6.7 | 5.2 | 2.7 | 85.4 |
| $Me_2$ | (0.5) | 8.9 | 76.0 | 3.2 | 1.7 | 19.1 |
| $S$[b] | (1.0) | 33.5 | 2.5 | 1.3 | 5.1 | 91.1 |
| $S$[b,c] | (1.0) | 35.0 | 74.2 | 1.8 | 0.7 | 23.3 |
| $(PhS)_2$ | (0.5) | 28.1 | — | 8.6 | 1.3 | 90.1 |
| $(PhS)_2$[c] | (0.5) | 61.7 | 57.4 | 0.5 | 0.2 | 41.9 |
| PhS~[c] | (0.5) | 56.1 | 24.8 | 0.2 | 0.3 | 74.7 |

[a] See Table I, Footnote a.
[b] Held at 10° C. for 7 hours instead of 3 hours.
[c] Not heated to 70° C.

EXAMPLE 8

Three different experiments were run in which the temperature was varied: 0°–5° C., 10°–15° C., and 20°–25° C. The results are shown in Table VII. The results at 0°–5° C. appear to be the most selective results; 10°–15° C. still appear to be very selective. When the temperature rises to 25° C. the yield drops and the reaction is much less selective.

The lower yield at the higher temperature is probably due to the fact that sulfonation competes with chlorination. The lower selectivity is probably due to the fact that when sulfonation competes with chlorination, there is excess sulfuryl chloride present which reacts with the 2,4,5-trichlorophenol to provide a higher amount of the 2,3,4,6-tetrachlorophenol.

TABLE VII

| Temperature (°C.) | Weight Yield (g) | Percent[a] A | B | C | D |
|---|---|---|---|---|---|
| 0–5 | 60.9 | — | 1.2 | 2.5 | 96.3 |
| 10–15 | 61.5 | — | 2.1 | 5.5 | 92.4 |
| 20–25 | 32.5 | 0.8 | 3.2 | 45.2 | 50.8 |

[a] See Table I, Footnote a

EXAMPLE 9

In this example three different modes of addition were used. The amounts of reactants were double that of the general procedure except for sulfuryl chloride, 89 g being the amount used. The reaction was kept between 5°–10° C. The results are all good, although the better selectivity appeared to be obtained when the dichlorophenol was added to the reaction mixture, either alone or with the sulfuryl chloride.

TABLE VIII

| Mode[a] | Weight Yield (g) | Percent[b] A | B | C | D |
|---|---|---|---|---|---|
| 1 | 121.4 | 0.4 | 0.9 | 3.2 | 95.5 |
| 2 | 122.1 | trace | 1.4 | 1.5 | 97.1 |
| 3 | 120.8 | trace | 0.5 | 5.6 | 93.9 |

[a] 1 2,5-Dichlorophenol was mixed with sulfuryl chloride and was added to the mixture of the remaining components as in the general procedure.
2 2,5-Dichlorophenol was dissolved in dimethyl sulfoxide and was added to the mixture of the remaining components.
3 Sulfuryl chloride was added to the mixture of the remaining components.
[b] See Table I, Footnote a.

We claim:

1. A process for manufacture of 2,4,5-trichlorophenol which comprises reacting 2,5-dichlorophenol with sulfuryl chloride in the presence of diphenylsulfide and sulfuric acid at a temperature between minus ten degrees centigrade (−10° C.) and twenty-five degrees centigrade (25° C.).

2. A process according to claim 1 wherein the temperature is between −10° C. and 20° C.

3. A process according to claim 2 wherein the sulfuric acid concentration is between 80% and 100%.

4. A process according to claim 3 wherein:
   (a) the moles of sulfuryl chloride used is between 0.9 and 1.3 times the moles of 2,5-dichlorophenol used,
   (b) the amount of diphenyl sulfide used is greater than 0.2 grams per mole of 2,5-dichlorophenol used, and
   (c) the concentration of sulfuric acid is between 85% and 98%.

5. A process according to claim 4 wherein the ratio of sulfuric acid to dicholorophenol used was from about 0.5:1 to 5:1 by weight.

6. A process according to claim 3 wherein:
   (a) the moles of sulfuryl chloride used is between 1.0 and 1.2 times the moles of 2,5-dichlorophenol used,
   (b) the temperature range is between 0° C. and 15° C.,
   (c) the amount of diphenyl sulfide used is greater than 0.2 grams per mole of 2,5-dichlorophenol used, and
   (d) the concentration of sulfuric acid is between 90% and 98%.

7. A process according to claim 6 wherein the ratio of sulfuric acid to dichlorophenol was from about 0.5:1 to 5:1 by weight.

8. A process according to claim 7 where 0.1 to 3.0 g of aluminum chloride per mole of dichlorophenol was used.

9. A process according to claim 8 wherein 20 ml to 70 ml of dimethyl sulfoxide per mole of dichlorophenol was used.

10. A process according to claims 5, 7 or 9 wherein the dichlorophenol was added to the sulfuric acid and diphenyl sulfide.

11. A process according to claims 5, 7 or 9 wherein the reaction mixture was heated to about 60° to 70° C. after the chlorination had finished.

* * * * *